United States Patent
Zhang (10) Patent No.: US 7,587,231 B2
(45) Date of Patent: Sep. 8, 2009

(54) WATER FAT SEPARATED MAGNETIC RESONANCE IMAGING METHOD AND SYSTEM USING STEADY-STATE FREE-PRECESSION

(75) Inventor: Weiguo Zhang, Foster City, CA (US)

(73) Assignee: Toshiba America MRI, Inc., Tustin, CA (US)

(*) Notice: Subject to any disclaimer, the term of this patent is extended or adjusted under 35 U.S.C. 154(b) by 697 days.

(21) Appl. No.: 10/753,342

(22) Filed: Jan. 9, 2004

(65) Prior Publication Data

US 2005/0171422 A1  Aug. 4, 2005

(51) Int. Cl.
*A61B 5/05* (2006.01)
(52) U.S. Cl. .................. 600/410; 324/307; 324/309
(58) Field of Classification Search ......... 600/407–480; 324/307, 309, 300, 312, 320, 308; 128/898
See application file for complete search history.

(56) References Cited

U.S. PATENT DOCUMENTS

| | | | |
|---|---|---|---|
| 5,055,790 A | 10/1991 | Siuciak et al. | |
| 5,225,781 A * | 7/1993 | Glover et al. | 324/309 |
| 5,245,282 A * | 9/1993 | Mugler et al. | 324/309 |
| 5,256,967 A | 10/1993 | Foo et al. | |
| 5,311,133 A | 5/1994 | Dannels | |
| 5,347,216 A | 9/1994 | Foo | |
| 5,352,979 A * | 10/1994 | Conturo | 324/307 |
| 5,404,882 A | 4/1995 | Santyr | |
| 5,420,510 A | 5/1995 | Fairbanks et al. | |
| 5,560,360 A | 10/1996 | Filler et al. | |
| 5,909,119 A | 6/1999 | Zhang et al. | |
| 6,091,243 A * | 7/2000 | Xiang et al. | 324/307 |
| 6,239,597 B1 | 5/2001 | McKinnon | |
| 6,263,228 B1 * | 7/2001 | Zhang et al. | 600/409 |
| 6,285,901 B1 | 9/2001 | Taicher et al. | |
| 6,307,368 B1 * | 10/2001 | Vasanawala et al. | 324/309 |
| 6,339,332 B1 * | 1/2002 | Deimling | 324/309 |
| 6,452,387 B1 | 9/2002 | Hargreaves et al. | |
| 6,459,922 B1 * | 10/2002 | Zhang | 600/410 |
| 6,493,569 B2 | 12/2002 | Foo et al. | |
| 6,552,542 B1 | 4/2003 | Overall | |
| 6,586,933 B1 | 7/2003 | Hardy et al. | |

(Continued)

FOREIGN PATENT DOCUMENTS

JP     2003-52667     2/2003

(Continued)

OTHER PUBLICATIONS

Yuval Zur et al., "An Analysis of Fast Imaging Sequences With Steady-State Transverse Magnetization Refocusing", Magnetic Resonance in Medicine 6, pp. 175-193 (1988).

(Continued)

*Primary Examiner*—Brian Casler
*Assistant Examiner*—Amanda L Lauritzen
(74) *Attorney, Agent, or Firm*—Nixon & Vanderhye PC (57) ABSTRACT

Water-fat separated magnetic resonance (MR) images with balanced steady-state free precession (SSFP) are produced. The acquired SSFP signals are isolated into multiple echo components in which the phase arrangements between the water and fat signals are controlled by appropriately selecting the TR and TE values of the SSFP imaging sequence. From the isolated echo components, the effects of the field inhomogeneities are corrected and water and fat images are separated.

10 Claims, 4 Drawing Sheets

U.S. PATENT DOCUMENTS

| | | | |
|---|---|---|---|
| 6,587,708 B2* | 7/2003 | Venkatesan et al. | 600/419 |
| 6,603,990 B2* | 8/2003 | Zhang et al. | 600/410 |
| 6,608,479 B1 | 8/2003 | Dixon et al. | |
| 6,624,630 B1 | 9/2003 | Foxall | |
| 6,841,997 B2* | 1/2005 | Feiweier | 324/307 |
| 6,856,134 B1* | 2/2005 | Reeder et al. | 324/309 |
| 6,922,054 B2* | 7/2005 | Hargreaves et al. | 324/307 |
| 7,020,509 B2* | 3/2006 | Heid | 600/410 |
| 7,068,031 B2* | 6/2006 | Miyoshi | 324/307 |
| 7,116,105 B1* | 10/2006 | Zhang | 324/307 |
| 7,176,683 B2* | 2/2007 | Reeder et al. | 324/307 |
| 7,233,818 B1* | 6/2007 | Aletras et al. | 600/410 |
| 7,253,620 B1* | 8/2007 | Derbyshire et al. | 324/307 |
| 7,349,729 B2* | 3/2008 | Reeder et al. | 600/410 |
| 2001/0010810 A1 | 8/2001 | Miyoshi | |
| 2002/0050816 A1 | 5/2002 | Miyoshi | |
| 2002/0082497 A1 | 6/2002 | Song | |
| 2002/0196019 A1 | 12/2002 | Yamazaki et al. | |
| 2003/0030435 A1 | 2/2003 | Venkatesan et al. | |
| 2003/0055329 A1 | 3/2003 | Zur | |
| 2003/0060697 A1 | 3/2003 | Zhang et al. | |
| 2003/0062893 A1 | 4/2003 | Overall | |
| 2003/0137298 A1 | 7/2003 | Yamazaki | |
| 2003/0160616 A1 | 8/2003 | Asano et al. | |
| 2003/0193337 A1 | 10/2003 | Meyer | |
| 2003/0210046 A1 | 11/2003 | Wind et al. | |
| 2004/0064035 A1* | 4/2004 | Miyoshi et al. | 600/410 |
| 2005/0165295 A1* | 7/2005 | Li et al. | 600/410 |
| 2006/0161060 A1* | 7/2006 | Pai | 324/309 |
| 2006/0220645 A1* | 10/2006 | Zhang | 324/309 |
| 2006/0250132 A1* | 11/2006 | Reeder et al. | 324/307 |
| 2007/0098298 A1* | 5/2007 | Xiang | 382/276 |
| 2007/0225591 A1* | 9/2007 | Derbyshire et al. | 600/410 |
| 2007/0285091 A1* | 12/2007 | Wen et al. | 324/309 |
| 2008/0012565 A1* | 1/2008 | McKenzie et al. | 324/309 |
| 2008/0012566 A1* | 1/2008 | Pineda et al. | 324/309 |
| 2008/0012567 A1* | 1/2008 | Yu et al. | 324/309 |

OTHER PUBLICATIONS

T.W. Redpath et al., "FADE-A New Fast Imaging Sequence", Magnetic Resonance in Medicine 6, pp. 224-234 (1988).

Y. Zur, "Motion-Insensitive, Steady-State Free Precession Imaging", Magnetic Resonance in Medicine 16, pp. 444-459 (1990).

Jeffrey L. Duerk et al, "Remember True FISP? A High SNR, Near 1-Second Imaging Method For T2-Like Contrast In Interventional MRI at .2 T", pp. 203-208 (JMRI 1998).

Shreyas S. Vasanawala, et al., "Linear Combination Steady-State Free Precession MRI", Magnetic Resonance In Medicine 34, pp. 82-90 (2000).

Klaus Scheffler et al. , "Magnetization Preparation During The Steady State: Fat-Saturated 3D TrueFISP", Magnetic Resonance In Medicine 45, pp. 1075-1080 (2001).

Shreyas et al., "Fluctuating Equilibrium MRI", Magnetic Resonance In Medicine 42, pp. 876-883 (1999).

S.S. Vasanawala et al., "Musculoskeletal Imaging With Phase Sensitive SSFP", Proc. Intl. Soc. Mag. Reson. Med. 11, p. 1487 (2003).

B.A. Hargreaves et al., "Fat Suppressed Steady-State Free Precession Imaging Using Phase Detection", Proc. Intl. Soc. Mag. Reson. Med. 11, p. 548 (2003).

S.B. Reeder et al., "Imaging Of Articular Cartilage at 3T With Multi-Point "Dixon" Fat-Water Separation and SSFP", Proc. Intl. Soc. Mag. Reson. Med. 11, p. 1515 (2003).

S.B. Reeder et al., "Multi-Coil "Dixon" Fat-Water Separation and SSFP Imaging", Proc. Intl. Soc. Mag. Reson. Med. 11, p. 698 (2003).

M. Miyoshi et al., "SSFP Fat Water Separation By Fourier Transfer Phase Cycling And The Single Quadrature Dixon Method", Proc. Intl. Soc. Mag. Reson. Med. 11, p. 981 (2003).

Dixon WT, "Simple Proton Spectroscopic Imaging", Radiology, Oct. 1984; 153(1):189-94. (Abstract Only).

Duane A. Yoder et al., "MRI Simulator With Static Field Inhomogeneity", pp. 1-12. (SPIE: Medical Imaging Conference 2002).

JPO Office Action dated Apr. 15, 2008 (with English translatin).

* cited by examiner

WATER FAT SEPARATED MAGNETIC RESONANCE IMAGING METHOD AND SYSTEM USING STEADY-STATE FREE-PRECESSION

BACKGROUND OF THE INVENTION

Magnetic resonance imaging (MRI) with fully refocused steady state free-precession (SSFP) provides efficient signal-to-noise (SNR) performance and good image contrast. However, the application of SSFP has been hindered by the periodic spectral response of the SSFP sequence that results in band artifacts dependent on static magnetic field ($B_0$) inhomogeneities and time of repetition (TR). In addition, strong signals from fat limit the clinical usefulness of SSFP images in many applications.

There is a long felt need for robust methods for water and fat separation with SSFP imaging in the presence of $B_0$ static magnetic field inhomogeneities. Methods that require no additional scans are preferable as they minimize scan time and avoid problems caused by inter-scan variations. It is also desirable to have SSFP imaging methods that are applicable in low-magnetic field and mid-field MRI systems.

BRIEF DESCRIPTION OF THE INVENTION

A robust SSFP imaging technique has been developed to separate water and fat in the presence of $B_0$ field inhomogeneities. This technique combines with phase-cycled SSFP to achieve water-fat separation as well as to eliminate (or at least reduce) band artifacts. The technique is applicable to magnetic fields having low-, mid- and high field strengths.

The invention, in one embodiment, is a phase-cycled SSFP imaging method with a time of repetition (TR) and a time to echo (TE) selected such that water and fat signals, after echo isolation, are orthogonal in one data set and anti-parallel in another data set. A phase correction map is generated from the anti-parallel data set. The phase correction map is applied to correct for $B_0$ field inhomogeneities in the orthogonal data set to yield images having good water-fat separation.

In a second embodiment, the invention is a phase-cycled SSFP imaging method which uses the commonly applied TR=2TE selection such that water and fat signals are orthogonal in all data after echo isolation. A combinatory signal is constructed from two of the separated echo signals and used to generate a phase correction map. The phase correction map is applied to correct for $B_0$ field inhomogeneities to yield finally water-fat separation.

In a third embodiment, the invention is a phase-cycled SSFP imaging method having an "assist scan" used in conjunction with a master sequence SSFP scan. The assist scan is a preliminary scan set to low spatial resolution so as to reduce its scan time. The TR and TE of the assist scan are selected such that water and fat signals are anti-parallel in at least one of the data sets after echo isolation. The anti-parallel data is used to generate a phase correction map that is used to correct for $B_0$ inhomogeneities in the master SSFP scan to yield images with good water-fat separation.

In a fourth embodiment, the invention is a phase-cycled SSFP imaging method which uses the commonly applied TR=2TE selection such that water and fat signals are significantly orthogonal in all data after echo isolation. A field map already available from the scanner is used to correct for $B_0$ field inhomogeneities and to yield water-fat separation.

DETAILED DESCRIPTION OF THE INVENTION

Magnetic Resonance Imaging (MRI) is a widely accepted and commercially available non-invasive technique for obtaining digitized visual images representing the internal structure of objects (such as the human body) having substantial populations of atomic nuclei that are susceptible to nuclear magnetic resonance (NMR) also known as magnetic resonance (MR) phenomena. In MRI, imposing a strong main magnetic field ($B_0$) on the nuclei polarizes nuclei in the body of a patient to be imaged.

The nuclei are excited by a radio frequency (RF) signal at characteristic NMR (Larmor) frequencies. By spatially distributing localized magnetic fields surrounding the body and analyzing the resulting RF responses from the nuclei, a map or image of these nuclei responses as a function of their spatial location is generated and displayed. An image of the nuclei responses provides a non-invasive view of a patient's internal organs and of other tissues.

Figure 1:
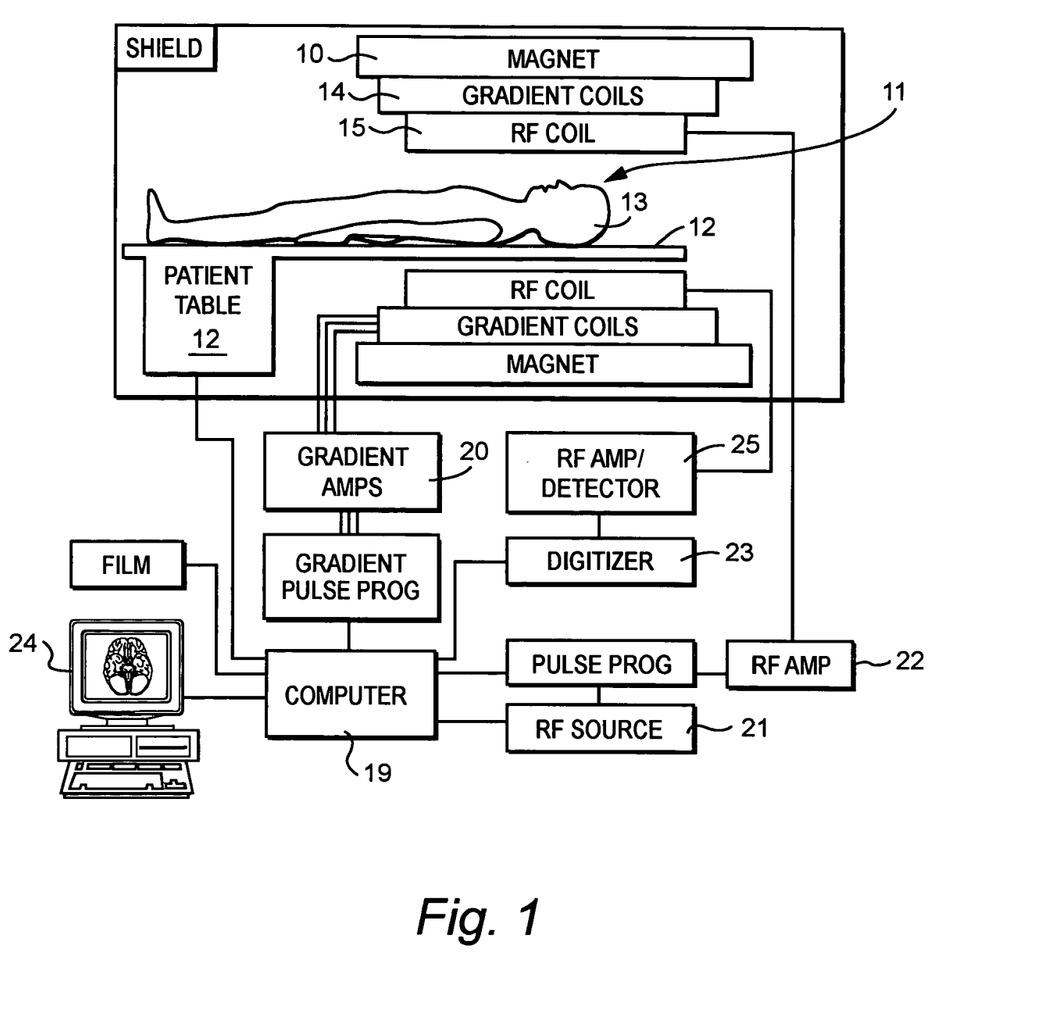
FIG. 1 is a schematic diagram of an MRI system.

As shown in FIG. 1, an MRI system typically includes a large magnet 10 to impose the static magnetic field ($B_0$), gradient coils 14 for imposing spatially distributed gradient magnetic fields ($G_x$, $G_y$, and $G_z$) along three orthogonal coordinates, and RF coils 15 and 16 to transmit and receive RF signals to and from the selected nuclei of the body being imaged. The patient 13 lies on a movable patient table 12 such that a portion of the patient to be imaged is moved, in three-dimensions, into an "imaging volume" 11 between the magnet and coils, which defines a field of view (FOV) of the MRI system.

Figure 2:
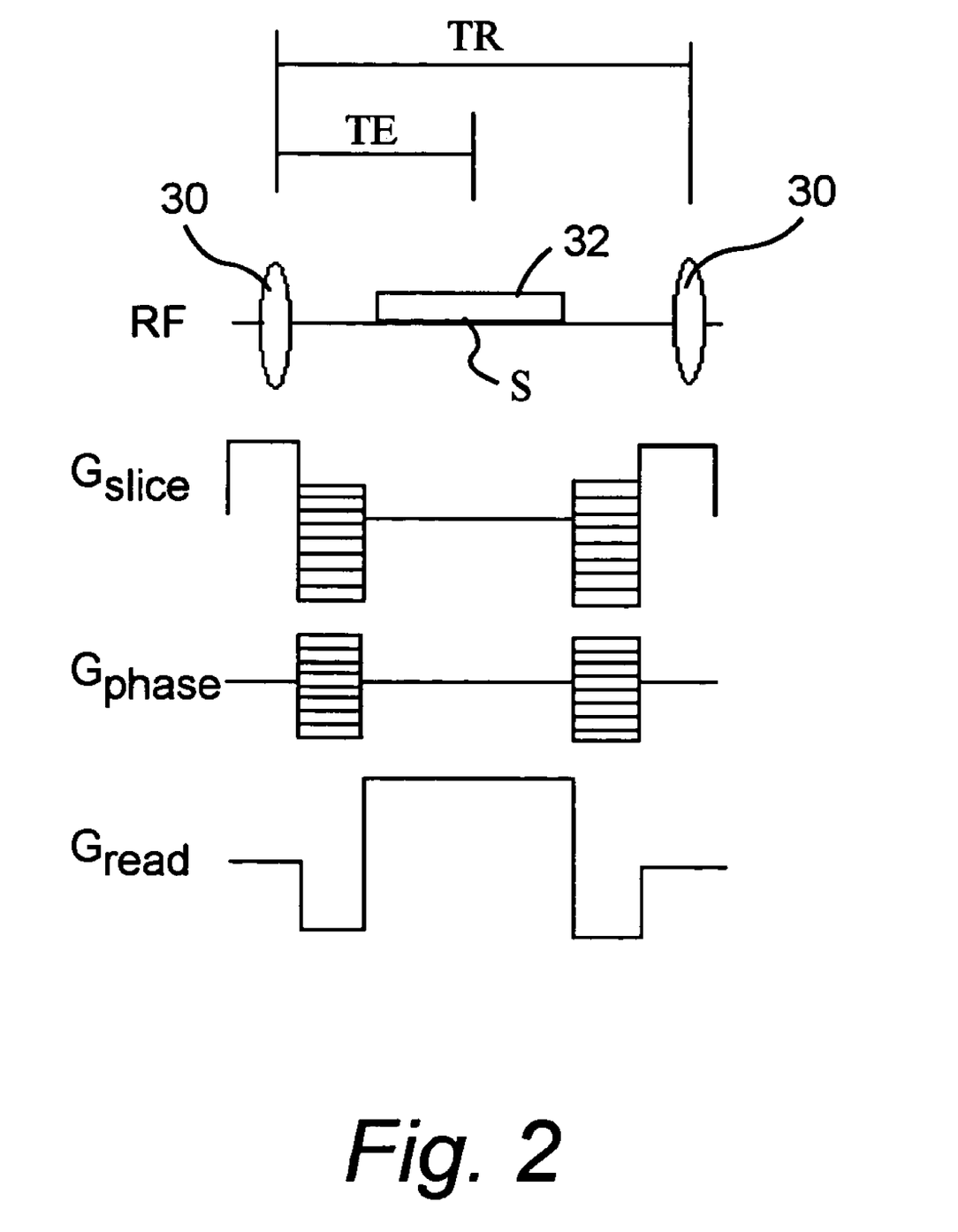
FIG. 2 is an exemplary SSFP sequence.

FIG. 2 schematically shows a three-dimensional (3D) magnetic resonance imaging sequence with fully refocused steady-state free precession (SSFP). A radio frequency (RF) excitation pulse 30 is applied to the body being scanned. The RF pulse 30 is periodically applied at a certain time of repetition (TR). An RF echo signal (S), is received during a data acquisition (ADC) period 32. The received echo signal occurs after a time to echo (TE) period that begins with the center of the RF pulse 30. Gradient magnetic fields are applied in the x, y and z directions to select and encode a set of slices ($G_{slice}$) of the body for imaging and to spatially phase encode ($G_{phase}$) the excited nuclei of the selected body slices. A readout magnetic field gradient ($G_{read}$) is applied during the ADC period to frequency-encode the received echo signal.

To acquire MRI data, the MRI system generates magnetic gradient and RF nutation pulses via MRI pulse sequence controllers 17 and 18 that operate under the control of a programmable processor 19, e.g., a workstation computer. In addition, the processor 19 controls gradient pulse amplifier 20, and RF source and amplifier circuits 21 and 22. The MR signal circuits (RF detector) 25 are suitably interfaced with MR signal RF coils 15, 16 located within the shielded MRI system gantry. The received MR RF echo signal responses are digitized by a digitizer 23 and passed to the processor 19, which may include an array processors or the like for image processing and suitable computer program storage media (not shown) wherein programs are stored and selectively utilized so as to control the acquisition and processing of MR signal data and to produce image displays on a CRT of control terminal 24. The MRI system control terminal 24 may include suitable keyboard switches and the like for exerting operator control. Images may also be recorded directly on film or on other suitable media by printing device.

Steady-state free precession (SSFP) is a conventional technique used to generate MRI signals from precessing hydrogen nuclei that do not completely return to their thermal equilibrium state. The SSFP sequence uses a series of RF excitation pulses and magnetic gradient pulses that are applied at repetition times (TR) significantly shorter than the spin-lattice (T1) and the spin-spin (T2) relaxation times of hydrogen nuclei within the subject being imaged. The magnetic gradient pulses are applied to reverse the magnetic field gradients in a predetermined manner to enhance the echo signal. In each TR period, the magnetic gradient pulses are fully balanced, i.e., the total areas of all gradient pulses are zero for each TR period.

MR signals acquired in a fully-refocused SSFP sequence, such as that shown in FIG. 2, comprise multiple echo sub-signals with different echo-formation pathways. The acquired MR signal, S, can be collectively represented as:

$$S = \sum_{n=-\infty}^{+\infty} S_n \qquad (1)$$

where $S_n$ denotes $n_{th}$ echo sub-signal. $S_0$, $S_{-1}$ and $S_1$ are the three most significant echo components. The echo sub-signals can be separated by RF phase cycling or frequency shifting. For a two component system of water and fat, the dominant echo sub-signals, $S_0$, $S_{-1}$ and $S_1$, can be described by $$S_0 = (W_0 + F_0 e^{i\psi_0}) e^{i\phi_0} \qquad (2)$$

$$S_{-1} = (W_{-1} + F_{-1} e^{i\psi_{-1}}) e^{i\phi_{-1}} \qquad (3)$$

$$S_1 = (W_1 + F_1 e^{i\psi_1}) e^{i\phi_1} \qquad (4)$$

where $$\psi_0 = 2\pi \Delta f TE \qquad (5)$$

$$\psi_{-1} = -2\pi \Delta f (TR - TE) \qquad (6)$$

$$\psi_1 = 2\pi \Delta f (TR + TE) \qquad (7)$$

$$\phi_0 = \gamma \Delta B_0 TE \qquad (8)$$

$$\phi_{-1} = -\gamma \Delta B_0 (TR - TE) \qquad (9)$$

$$\phi_1 = \gamma \Delta B_0 (TR + TE) \qquad (10)$$

wherein $W_0$ and $F_0$ are amplitudes of water and fat signals, respectively, in $S_0$; $W_{-1}$ and $F_{-1}$ are amplitudes of water and fat signals, respectively, in $S_{-1}$; $W_1$ and $F_1$ are amplitudes of water and fat signals, respectively, in $S_1$; $\Delta B_0$ represents $B_0$ inhomogeneities; TR and TE are repetition and echo times, respectively, of the SSFP sequence, such as shown in FIG. 2; and $\Delta f$ is the difference in resonance frequency between the water and fat signals.

As shown in equations (2-10), $S_0$, $S_{-1}$ and $S_1$ are modulated differently by the chemical shift and $B_0$ field inhomogeneities depending on the values of TR and TE. This modulation difference can be harvested to assist with the separation of water and fat data.

A phase-cycled or frequency-shifted SSFP sequence is used to acquire signals that can be isolated into sub-signals ($S_0$, $S_{-1}$, $S_1$, etc.) to yield artifact-free images. Phase-cycled or frequency-shifted SSFP, and isolation of the signals are conventional and well-known in the prior art. The isolated sub-signals are applied to achieve water-fat separation that are free of banding artifacts and provide good water-fat separation in the presence of $B_0$ field inhomogeneities.

Figure 3:
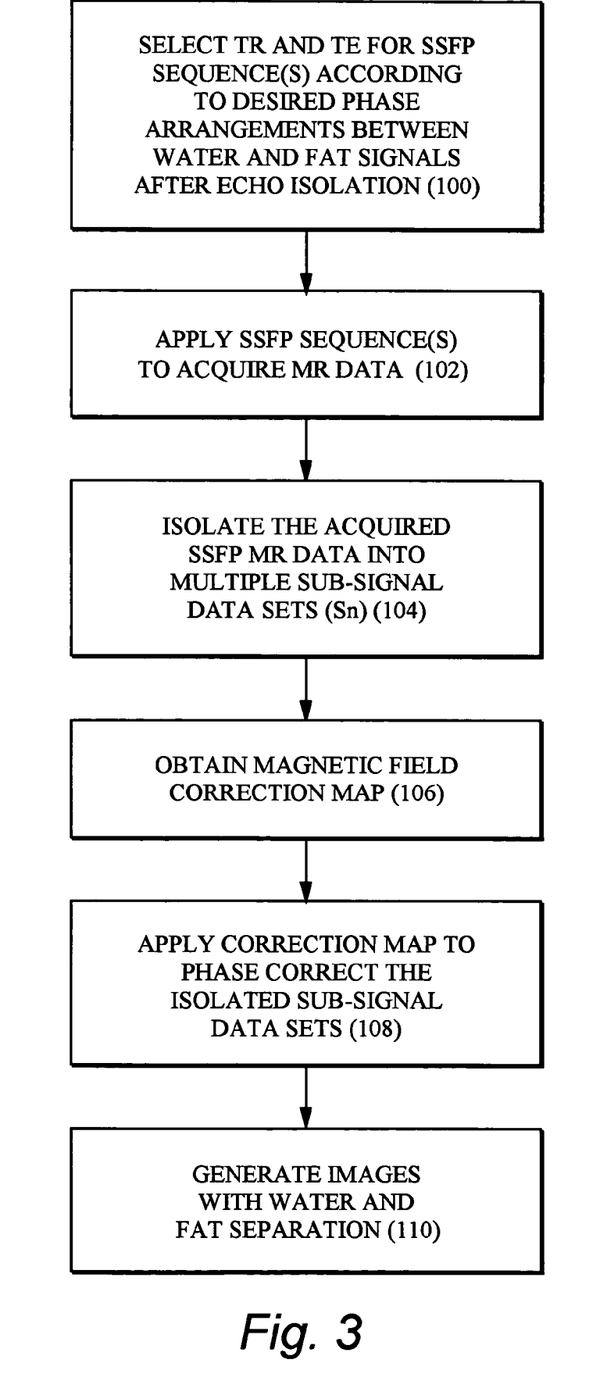
FIG. 3 is a flow chart of steps for acquiring SSFP data from which a phase correction map is generated and used to yield water-fat separated SSFP images.

FIG. 3 is a flow chart of process steps to be performed in order to separate water and fat images. SSFP signals can be acquired for purposes of water-fat separation in at least four manners, briefly:

First—Single SSFP Scan: Select TR and TE of the SSFP scan sequence so that water and fat signals are orthogonal in $S_0$ and anti-parallel in $S_{-1}$, or vice versa, in step 100. An SSFP scan is performed, 102, with the selected TR and TE values to obtain echo signals from a body. The echo signals are separated into orthogonal $S_0$ and anti-parallel $S_{-1}$ data sets, in step 104. A magnetic field map is generated from the anti-parallel data in step 106. The field map is applied as a phase correction factor to the orthogonal data set(s), in step 108. Water and fat images can be constructed from the orthogonal data after applying the phase correction to compensate for $B_0$ field inhomogeneities, in step 110.

Second—Single SSFP Scan: Select TR and TE of the SSFP scan sequence with TR equal to 2TE and such that water and fat signals are orthogonal in all separated signals, 100. Apply the imaging sequence and acquire MR data, 102. Isolate the acquired SSFP MR data to have $S_{-1}$, $S_0$, and $S_1$, 104. Generate a field map from a combinatory signal of $S_0 S_1$, 106. Generate water-fat images constructed from $S_0$ and $S_{-1}$, 110, after applying the field map for phase correction, 108.

Third—Assist and Master SSFP Scans: Select TR and TE for a master SSFP scan sequence, $TR^m$ and $TE^m$, such that water and fat signals are significantly orthogonal in all separated signals, 100. Select TR and TE for a low spatial resolution "assist scan" sequence, $TR^a$ and $TE^a$, such that water and fat signals are anti-parallel in at least one of the separated signals, 100. Apply both the "master" scan and the "assist" scan in a single session, 102. Generate a field map from the anti-parallel data of the "assist" scan, 106. The water-fat images are constructed from the master scan data, 110, to which the field map from the "assist" scan is applied for phase correction, 108.

Fourth—Single SSFP Scan with Known Field Map: Select TR and TE for an SSFP sequence such that water and fat signals are significantly orthogonal in all separated signals, 100. Apply the imaging sequence to acquire MR data, 102. Isolate the acquired SSFP MR data to have $S_0$ and $S_{-1}$, 104. Obtain a magnetic field map available from the scanner, 106. Apply the field map to phase-correct $S_0$ and $S_-$, 108, and generate images with water-fat separation, 110.

In a first embodiment, TR and TE are selected so that water and fat signals are orthogonal in $S_0$ and anti-parallel in $S_{-1}$. This can be accomplished, for example, by selecting TR and TE according to:

$$TE = (2j+1)/(4\Delta f) \text{ and } TR = (6j+3)/(4\Delta f), j=0, 1, 2, \qquad (11)$$

At 0.35 Telsa, one such selection corresponds to TR=15 milliseconds (ms) and TE=5 ms (j=0). The acquired SSFP signals after echo isolation can be described as:

$$S_0 = (W_0 + iF_0) e^{i\phi} \qquad (12)$$

$$S_{-1}=(W_{-1}-F_{-1})e^{-i2\phi} \quad (13)$$

A field correction map can be estimated from $S_{-1}$ according to the following relationship:

$$-4\phi=\text{unwrap}\{\arg(S_{-1}^2)\} \quad (14)$$

where unwrap{ } stands for the mathematical process for phase-unwrapping such as is described in U.S. Pat. No. 5,909,119, (which is incorporated by reference) and arg( ) returns the principle phase value of its complex input.

Correcting the $S_0$ image by the phase correction map yields:

$$S_0^{corr}=S_0 e^{-i\phi}=W_0+iF_0 \quad (15)$$

and water-fat images can finally be constructed directly from $S_0^{corr}$ according to:

$$I_W=|\text{real}\{S_0^{corr}\}| \quad (16)$$

$$I_F=|\text{imag}\{S_0^{corr}\}| \quad (17)$$

where real{ } and imag{ } stand for mathematical routines for returning the real and imaginary part, respectively, of the complex input.

In a second embodiment, TR and TE are selected according to a commonly used TR=2TE condition such that water and fat signals are orthogonal in all isolated echo signals. This can be accomplished by selecting TR=2TE=(2j+1)/(2Δf) with j=0, 1, 2, . . . At 0.35 T, one such selection corresponds to TR=10 ms, TE=5 ms. After isolation, the echo signals, can be described as:

$$S_0=(W_0+iF_0)e^{i\phi} \quad (18)$$

$$S_{-1}=(W_{-1}-iF_{-1})e^{-i\phi} \quad (19)$$

$$S_1=(W_1-iF_1)e^{i3\phi} \quad (20)$$

A combinatory signal is constructed using the following relationship:

$$S_0 S_1 = [(W_0 W_1 + F_0 F_1) + i(F_0 W_1 - W_0 F_1)]e^{i4\phi} \quad (21)$$

Since it is mostly true that $|W_0 W_1 + F_0 F_1| >> |F_0 W_1 - W_0 F_1|$, $S_0 S_1$ can be approximated by $$S_0 S_1 \cong (W_0 W_1 + F_0 F_1)e^{i4\phi}, \quad (22)$$

meaning that the phase of the combinatory signal is dominated by the inhomogeneity angle ($\phi$). A field correction map can be generated according to:

$$4\phi=\text{unwrap}\{\arg(S_0 S_1)\} \quad (23)$$

The $S_0$ and $S_{-1}$ images are phase-corrected using the field correction map (4$\phi$) and used to finally yield water and fat images ($I_w$ and $I_f$ respectively) described as follows:

$$S_0^{corr}=S_0 e^{-i\phi}=W_0+iF_0 \quad (24)$$

$$S_{-1}^{corr}=S_{-1}e^{i\phi}=W_{-1}-iF_{-1} \quad (25)$$

$$I_W=|\text{real}(S_0^{corr})| \quad (26)$$

$$I_F=|\text{imag}(S_0^{corr})| \quad (27)$$

or $$I_W=|\text{real}(S_{-1}^{corr})| \quad (28)$$

$$I_F=|\text{imag}(S_{-1}^{corr})| \quad (29)$$

or $$I_W=\frac{1}{2}|\text{real}(S_0^{corr})|+\frac{1}{2}|\text{real}(S_{-1}^{corr})| \quad (30)$$

$$I_F=\frac{1}{2}|\text{imag}(S_0^{corr})|+\frac{1}{2}|\text{imag}(S_{-1}^{corr})| \quad (31)$$

In a third embodiment, a phase-cycled SSFP master scan is accompanied with a low spatial resolution "assist" scan. For the assist scan, the TR and TE values, $TR^a$ and $TE^a$, are selected such that water and fat signals are orthogonal in $S_0$ and anti-parallel in $S_{-1}$. The TR and TE values, $TR^m$ and $TE^m$, are selected for the master scan such that water and fat signals are significantly orthogonal in both $S_0$ and $S_{-1}$. We therefore have:

$$S_0^a=(W_0^a+iF_0^a)e^{i\phi_0^a} \quad (32)$$

$$S_{-1}^a=(W_{-1}^a-F_{-1}^a)e^{-i\phi_{-1}^a} \quad (33)$$

$$S_0^m=(W_0^m+F_0^m e^{i\psi_0^m})e^{i\phi_0^m} \quad (34)$$

$$S_{-1}^m=(W_{-1}^m+F_{-1}^m e^{-i\psi_{-1}^m})e^{-i\phi_{-1}^m} \quad (35)$$

where $$\phi_0^a=\gamma\Delta B_0 TE^a \quad (36)$$

$$\phi_{-1}^a=\gamma\Delta B_0(TR^a-TE^a) \quad (37)$$

$$\phi_0^m=\gamma\Delta B_0 TE^m \quad (38)$$

$$\phi_{-1}^m=\gamma\Delta B_0(TR^m-TE^m) \quad (39)$$

$$\psi_0^m=2\pi\Delta f TE^m \quad (40)$$

$$\psi_{-1}^m=2\pi\Delta f(TR^m-TE^m) \quad (41)$$

A low spatial resolution field correction map is generated from $S_{-1}^a$ according to:

$$-2\phi_{-1}^a=\text{unwrap}\{\arg(S_{-1}^a \cdot S_{-1}^a)\} \quad (42)$$

The correction map is applied to correct the isolated echo images from the master scan to yield:

$$S_0^{m,corr}=S_0^m e^{-i\phi_{-1}^a\left(\frac{TE^m}{TR^a-TE^a}\right)}=W_0^m+F_0^m e^{i\psi_0^m} \quad (43)$$

$$S_{-1}^{m,corr}=S_{-1}^m e^{-i\phi_{-1}^a\left(\frac{TR^m-TE^m}{TR^a-TE^a}\right)}=W_{-1}^m+F_{-1}^m e^{-i\psi_{-1}^m} \quad (44)$$

Water and fat images can be constructed according to:

$$I_W=|\text{Real}(S_0^{m,corr})-\text{Imag}(S_0^{m,corr})\cdot\cot(\psi_0^m)| \quad (45)$$

$$I_F=\left|\frac{\text{Imag}(S_0^{m,corr})}{\sin(\psi_0^m)}\right| \quad (46)$$

or $$I_W=|\text{Real}(S_{-1}^{m,corr})-\text{Imag}(S_{-1}^{m,corr})\cdot\cot(\psi_{-1}^m)| \quad (47)$$

$$I_F = \left| \frac{\text{Imag}(S_{-1}^{m,corr})}{\sin(\psi_{-1}^m)} \right| \quad (48)$$

or $$I_W = \frac{1}{2} |\text{Real }(S_0^{m,corr}) - \text{Imag}(S_0^{m,corr}) \cdot \cot(\psi_0^m)| + \quad (49)$$
$$\frac{1}{2} |\text{Real }(S_{-1}^{m,corr}) - \text{Imag}(S_{-1}^{m,corr}) \cdot \cot(\psi_{-1}^{m,corr})|$$

$$I_F = \frac{1}{2} \left| \frac{\text{Imag}(S_0^{corr})}{\sin(\psi_0^m)} \right| + \frac{1}{2} \left| \frac{\text{Imag}(S_{-1}^{corr})}{\sin(\psi_{-1}^m)} \right| \quad (50)$$

In a fourth embodiment, when a field map of the scanner is available for use, TR and TE are selected for a phase-cycled SSFP imaging sequence such that water and fat signals are significantly orthogonal in all sub-signals after echo isolation. The isolated echo signals are phase-corrected by the field map ($\Delta B_0$), that is available either from a prior session of field shimming or from another procedure that measures the magnetic field distribution. Water and fat images are constructed from the phase-corrected sub-signals according to:

$$S_0^{corr} = S_0 e^{-i\gamma \Delta B_0 TE} = (W_0 + F_0 e^{i2\pi \Delta f TE}) \quad (51)$$

$$S_{-1}^{corr} = S_{-1} e^{i\gamma \Delta B_0 (TR-TE)} = (W_{-1} + F_{-1} e^{-i2\pi \Delta f(TR-TE)}) \quad (52)$$

$$I_W = |\text{Real}(S_0^{corr}) - \text{Imag}(S_0^{corr}) \cdot \cot(2\pi \Delta f TE)| \quad (53)$$

$$I_F = \left| \frac{\text{Imag}(S_0^{corr})}{\sin(2\pi \Delta f TE)} \right| \quad (54)$$

or $$I_W = |\text{Real}(S_{-1}^{corr}) - \text{Imag}(S_{-1}^{corr}) \cdot \cot(2\pi \Delta f(TR-TE))| \quad (55)$$

$$I_F = \left| \frac{\text{Imag}(S_{-1}^{corr})}{\sin(2\pi \Delta f(TR-TE))} \right| \quad (56)$$

or $$I_W = \frac{1}{2} |\text{Real }(S_0^{m,corr}) - \text{Imag}(S_0^{m,corr}) \cdot \cot(2\pi \Delta f TE)| + \quad (57)$$
$$\frac{1}{2} |\text{Real }(S_{-1}^{m,corr}) - \text{Imag}(S_{-1}^{m,corr}) \cdot \cot(2\pi \Delta f(TR-TE))|$$

$$I_F = \frac{1}{2} \left| \frac{\text{Imag}(S_0^{corr})}{\sin(2\pi \Delta f TE)} \right| + \frac{1}{2} \left| \frac{\text{Imag}(S_{-1}^{corr})}{\sin(2\pi \Delta f(TR-TE))} \right| \quad (58)$$

Figure 4:
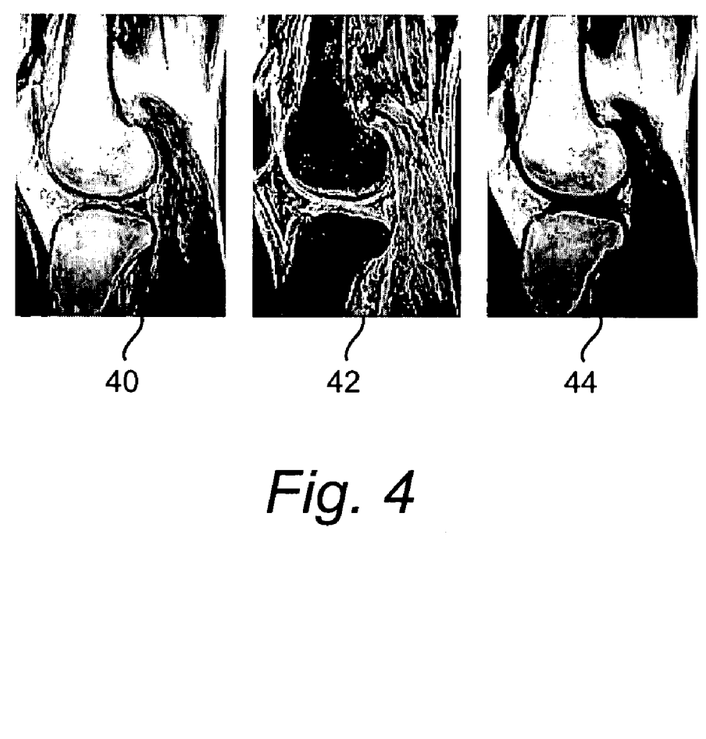
FIGS. 4 and 5 are each a series of images acquired and processed using the techniques described herein.

FIG. 4 are computer-generated images showing water and fat separated SSFP images generated according to the first embodiment of the invention. The phase-cycled SSFP imaging sequence had TE of 5 ms and TR of 15 ms. The phase of the RF pulse was incremented by 0, 60, 120, 180, 240, and 300 degrees, respectively. The left image 40 is the isolated SSFP image of $S_0$. The middle image 42 shows the separated water data. The right image 44 shows the separated fat data. These images show an absence of banding and a high quality of water-fat separation achieved.

Figure 5:
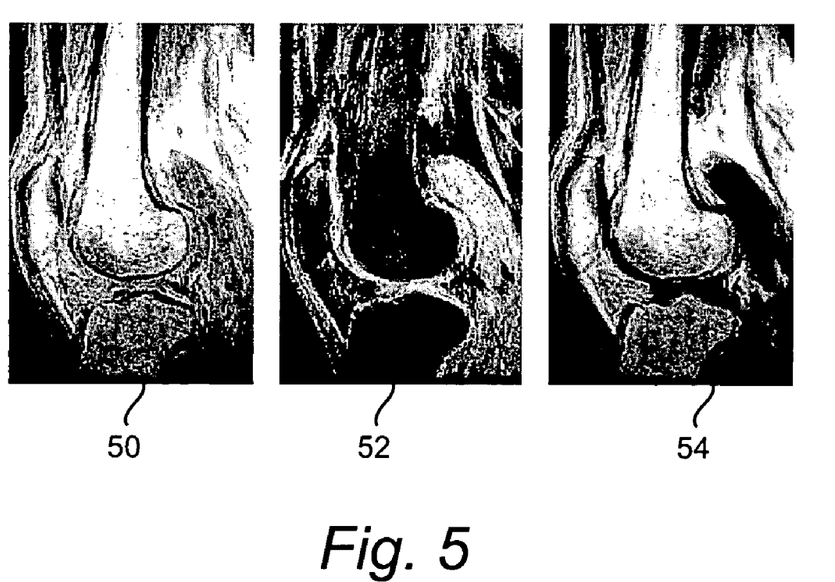

FIG. 5 shows the combined image of $S_0$ and $S_{-1}$ 50, separated water 52 and fat 54 SSFP images generated according to the second embodiment. The phase-cycled SSFP imaging sequence had a TE of 5 ms and TR of 10 ms. The phase of the RF pulse was incremented by 0, 60, 120, 180, 240, and 300 degrees, respectively. While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of separating and identifying water and fat magnetic resonance (MR) images of a body with balanced steady state free-precession (SSFP), said method comprising: using an MRI apparatus to:
   (a) select a time of repetition (TR) and a time to echo period (TE) for a phase-cycled SSFP sequence in accordance with a desired water-fat phase arrangement for echo components after isolation, said echo components respectively corresponding to different echo-formation pathways and containing signals emanating from both fat and water nuclei;
   (b) apply the SSFP sequence with the selected TR and TE at said selected values to obtain MR SSFP data from the body being imaged;
   (c) isolate the acquired SSFP data into multiple of said echo components in which water and fat signals have the desired phase arrangements;
   (d) generate a field correction map from the isolated echo components data or using a field map already available from the MRI apparatus;
   (e) apply the field correction map to correct the isolated echo components data wherein water and fat signals in the data are orthogonal or substantially orthogonal; and
   (f) generate water and fat images from the phase-corrected isolated echo components data.

2. A method as in claim 1 wherein the TR and the TE are selected such that water and fat signals are orthogonal in $S_0$ and anti-parallel in $S_{-1}$ after echo isolation.

3. A method as in claim 2 further comprising:
   using said MRI apparatus to:
   (g) apply the SSFP sequence with the selected TR and TE to obtain MR SSFP data from the body being imaged;
   (h) isolate the SSFP data to have $S_0$ and $S_{-1}$, wherein water and fat signals are orthogonal in $S_0$ and anti-parallel in $S_{-1}$;
   (i) generate a field correction map from $S_{-1}$ according to:

$$-2\phi = \text{unwrap }\{\arg(S_{-1}^2)\};$$

(j) apply the field map to correct $S_0$ to have:

$$S_0^{corr} = S_0 e^{-i\phi \frac{TE}{TR-TE}}$$

; and
   (k) generate water and fat images from $S_0^{corr}$ according to:

$$I_W = |\text{real }\{S_0^{corr}\}|$$

$$I_F = |\text{imag }\{S_0^{corr}\}|.$$

4. A method as in claim 1 wherein the TR and TE are selected with TR=2TE and such that water and fat signals are orthogonal in all echo components after isolation.

5. A method as in claim 4 further comprising:
   using said MRI apparatus to:
   (g) apply the SSFP sequence with the selected TR and TE to obtain MR SSFP data from the body being imaged;
   (h) isolate the SSFP data to have $S_{-1}$, $S_0$ and $S_1$, wherein water and fat signals are orthogonal;
   (i) construct a combinatory data of $S_0 \cdot S_1$;

(j) generate a field correction map from the combinatory data according to:

$$4\phi = \text{unwrap}\{\arg(S_0 \cdot S_1)\}$$

(k) apply the field correction map to correct $S_{-1}$ and $S_0$ to have:

$$S_0^{corr} = S_0 e^{-i\phi}$$

$$S_{-1}^{corr} = S_{-1} e^{i\phi}$$

(l) generating water and fat images from $S_0^{corr}$ and/or $S_{-1}^{corr}$ according to at least one of:

$$I_W = |\text{real}(S_0^{corr})|$$

$$I_F = |\text{imag}(S_0^{corr})|$$

and $$I_W = |\text{real}(S_{-1}^{corr})|$$

$$I_F = |\text{imag}(S_{-1}^{corr})|$$

and $$I_W = \frac{1}{2}|\text{real}(S_0^{corr})| + \frac{1}{2}|\text{real}(S_{-1}^{corr})|$$

$$I_F = \frac{1}{2}|\text{imag}(S_0^{corr})| + \frac{1}{2}|\text{imag}(S_{-1}^{corr})|.$$

6. A method as in claim 1 wherein a master phase-cycled SSFP sequence is accompanied with a low spatial resolution assist SSFP imaging sequence.

7. A method as in claim 6 wherein TR and TE of the master SSFP sequence, designated herein as $TR^m$ and $TE^m$ respectively, are selected with $TR^m$ equal to $2TE^m$ and such that water and fat signals are substantially orthogonal in all echo components, and TR and TE of the assist SSFP imaging sequence, herein designated as $TR^a$ and $TE^a$ respectively, are selected such that water and fat signals are anti-parallel in $S_{-1}$ after echo isolation.

8. A method as in claim 7 further comprising:

using said MRI apparatus to:

(g) apply both the master SSFP sequence and the assist SSFP imaging sequence with the selected TR and TE combinations to obtain MR data from the body being imaged;

(h) isolate the SSFP data to have $S_0^m$ and $S_{-1}^m$ from the master scan data, and $S_{-1}^a$ from the assist scan data;

(i) generate a field correction map from $S_{-1}^a$ according to:

$$-2\phi = \text{unwrap}\{\arg(S_{-1}^a \cdot S_{-1}^a)\};$$

(j) apply the field correction map to correct $S_0^m$ and $S_{-1}^m$ of the master scan data to have:

$$S_0^{m,corr} = S_0 e^{-i\phi \frac{TE^m}{TR^a - TE^a}}$$

$$S_{-1}^{m,corr} = S_{-1} e^{i\phi \frac{TR^m - TE^m}{TR^a - TE^a}};$$

and (k) generate water and fat images from at least one of $S_0^{m,corr}$ and $S_{-1}^{m,corr}$ according to at least one of:

$$I_W = |\text{Real}(S_0^{m,corr}) - \text{Imag}(S_0^{m,corr}) \cdot \cot(\psi_0^m)|$$

$$I_F = \left|\frac{\text{Imag}(S_0^{m,corr})}{\sin(\psi_0^m)}\right|$$

and $$I_W = |\text{Real}(S_{-1}^{m,corr}) - \text{Imag}(S_{-1}^{m,corr}) \cdot \cot(\psi_{-1}^m)|$$

$$I_F = \left|\frac{\text{Imag}(S_{-1}^{m,corr})}{\sin(\psi_{-1}^m)}\right|$$

and $$I_W = \frac{1}{2}\left|\text{Real}(S_0^{m,corr}) - \text{Imag}(S_0^{m,corr}) \cdot \cot(\psi_0^m)\right| + \frac{1}{2}\left|\text{Real}(S_{-1}^{m,corr}) - \text{Imag}(S_{-1}^{m,corr}) \cdot \cot(\psi_{-1}^m)\right|$$

$$I_F = \frac{1}{2}\left|\frac{\text{Imag}(S_0^{m,corr})}{\sin(\psi_0^m)}\right| + \frac{1}{2}\left|\frac{\text{Imag}(S_{-1}^{m,corr})}{\sin(\psi_{-1}^m)}\right|$$

with $$\psi_0^m = 2\pi\Delta f TE^m$$

$$\psi_{-1}^m = 2\pi\Delta f(TR^m - TE^m).$$

9. A method as in claim 1 wherein TR and TE are selected with TR equal to 2 times TE, and such that water and fat signals are significantly orthogonal in all echo components after echo isolation.

10. A method as in claim 9 further comprising:

using said MRI apparatus to:

(g) applying the SSFP sequence with the selected TR and TE to obtain MR data from the body being imaged;

(h) isolating the SSFP data to have $S_0$ and $S_{-1}$ echo components;

(i) obtaining a $B_0$ field map, $\Delta B_0$, that is available from the scanner;

(j) applying the $B_0$ field map to $S_0$ and $S_{-1}$ to have:

$$S_0^{corr} = S_0 e^{-i\gamma \Delta B_0 TE}$$

$$S_{-1}^{corr} = S_{-1} e^{i\gamma \Delta B_0 (TR-TE)}; \text{ and}$$

(k) generating water and fat images from at least one of $S_0^{corr}$ and $S_{-1}^{corr}$ according to at least one of:

$$I_W = |\text{Real}(S_0^{corr}) - \text{Imag}(S_0^{corr}) \cdot \cot(2\pi\Delta f TE)|$$

$$I_F = \left|\frac{\text{Imag}(S_0^{corr})}{\sin(2\pi\Delta f TE)}\right|$$

and $$I_W = |\text{Real}(S_{-1}^{corr}) - \text{Imag}(S_{-1}^{corr}) \cdot \cot(2\pi\Delta f(TR-TE))|$$

$$I_F = \left|\frac{\text{Imag}(S_{-1}^{corr})}{\sin(2\pi\Delta f(TR - TE))}\right|$$

and $$I_W = \frac{1}{2}\left|\text{Real}(S_0^{corr}) - \text{Imag}(S_0^{corr}) \cdot \cot(2\pi\Delta f TE)\right| + \frac{1}{2}\left|\text{Real}(S_{-1}^{corr}) - \text{Imag}(S_{-1}^{corr}) \cdot \cot(2\pi\Delta f(TR - TE))\right|$$

-continued
$$I_F = \frac{1}{2}\left|\frac{\text{Imag}(S_0^{corr})}{\sin(2\pi\Delta f TE)}\right| + \frac{1}{2}\left|\frac{\text{Imag}(S_{-1}^{corr})}{\sin(2\pi\Delta f(TR-TE))}\right|.$$

\* \* \* \* \*